(12) United States Patent
Fukushima et al.

(10) Patent No.: US 7,748,281 B2
(45) Date of Patent: Jul. 6, 2010

(54) DISPENSING APPARATUS, DISPENSING METHOD, AND ANALYZER

(75) Inventors: Norichika Fukushima, Tokyo (JP); Shigeru Yoshinari, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 195 days.

(21) Appl. No.: 11/951,632

(22) Filed: Dec. 6, 2007

(65) Prior Publication Data
US 2008/0236301 A1 Oct. 2, 2008

Related U.S. Application Data

(63) Continuation of application No. PCT/JP2006/310802, filed on May 30, 2006.

(30) Foreign Application Priority Data

Jun. 9, 2005 (JP) ............................. 2005-170129
Jun. 9, 2005 (JP) ............................. 2005-170130

(51) Int. Cl.
*G01N 1/14* (2006.01)
(52) U.S. Cl. .................................. 73/864.13
(58) Field of Classification Search ............. 73/863.01, 73/863.33, 864.11, 864.16; 222/23
See application file for complete search history.

(56) References Cited

U.S. PATENT DOCUMENTS 4,475,666 A * 10/1984 Bilbrey et al. .................. 222/14
5,965,828 A    10/1999 Merriam
6,158,269 A * 12/2000 Dorenkott et al. ............... 73/37

FOREIGN PATENT DOCUMENTS

| JP | 07-333231 | 12/1995 |
| JP | 2000-65843 | 3/2000 |
| JP | 2000-513109 | 10/2000 |

* cited by examiner

*Primary Examiner*—Hezron Williams
*Assistant Examiner*—Nathaniel Kolb
(74) *Attorney, Agent, or Firm*—Townsend and Townsend and Crew LLP

(57) ABSTRACT

A dispensing apparatus includes a syringe which has a piston and sucks and discharges a liquid; and a storage unit which stores therein a reference driving profile indicating a reference of a driving position and a driving time at starting the piston. The apparatus also includes a position detector which detects an actual driving position of the piston; a timer which measures an actual driving time of the piston; and a driving controller which controls driving of the piston based on the reference driving profile, the driving controller creating an actual driving profile based on the actual driving position and the actual driving time of the piston, and the driving controller comparing the reference driving profile with the actual driving profile to determine based on a result of the comparing whether the dispensing is proper or not.

25 Claims, 7 Drawing Sheets

| VISCOSITY: 1.0 [mPa·s] | | | | |
|---|---|---|---|---|
| DISPENSING AMOUNT [nL] | MOVING DISTANCE [mm] | MOTION STARTING POSITION | MOTION STOPPING POSITION | REFERENCE VELOCITY PROFILE |
| 100 | 3.18 | 10 | 13.18 | A |
| 90 | 2.86 | 5 | 7.86 | A |
| 80 | 2.54 | 2 | 4.54 | A |
| ⋮ | ⋮ | ⋮ | ⋮ | ⋮ |
| 10 | 0.32 | 1 | 1.32 | B |

DISPENSING APPARATUS, DISPENSING METHOD, AND ANALYZER

CROSS-REFERENCE TO RELATED APPLICATIONS

This application is a continuation of PCT international application Ser. PCT/JP2006/310802 filed May 30, 2006 which designates the United States, incorporated herein by reference, and which claims the benefit of priority from Japanese Patent Applications No. 2005-170130 and No. 2005-170129, both filed Jun. 9, 2005, incorporated herein by reference.

BACKGROUND OF THE INVENTION

1. Field of the Invention

The present invention relates to a dispensing apparatus and a dispensing method in which a syringe having a piston performs a liquid sucking/discharging operation to dispense the liquid, and to an analyzer.

2. Description of the Related Art

Conventionally, a dispensing apparatus which drives a piston to suck liquid into a syringe and discharge the liquid from the syringe (see Japanese Patent Application Laid-Open No. H7-333231), and an analyzer including the dispensing apparatus have been known. The piston is generally connected to a rotation motor via a rotation-translation converting mechanism such as a ball screw, and a translatory movement converted from a rotational movement of the rotation motor allows a liquid sucking/discharging operation. The dispensing apparatus controls the rotation of the rotation motor to control the liquid dispensing operation.

However, in such a dispensing apparatus using the syringe, the amount of liquid dispensed from the syringe varies depending not only on a moving distance of the piston but also on other conditions. Therefore, the dispensing apparatus only with a setting of the moving distance of the piston has a variation in the amount of liquid dispensed from the syringe. Such a variation in the dispensed liquid amount causes, in some cases, an incorrect analysis on the liquid in the dispensing apparatus.

SUMMARY OF THE INVENTION

A dispensing apparatus according to one aspect of the present invention includes a syringe which has a piston, the syringe sucking and discharging a liquid; a storage unit which stores therein a reference driving profile indicating a reference of a driving position and a driving time at starting the piston; a position detector which detects an actual driving position of the piston; a timer which measures an actual driving time of the piston; and a driving controller which controls driving of the piston based on the reference driving profile, the driving controller creating an actual driving profile based on the actual driving position and the actual driving time of the piston, and the driving controller comparing the reference driving profile with the actual driving profile to determine based on a result of the comparing whether the dispensing is proper or not.

A dispensing method according to another aspect of the present invention is for dispensing a liquid, in which a syringe having a piston, the syringe sucking and discharging the liquid, and includes storing a reference driving profile indicating a reference of a driving position and a driving time at starting the piston; detecting an actual driving position of the piston; a measuring step of measuring an actual driving time of the piston; controlling driving of the piston based on the reference driving profile; creating an actual driving profile based on the actual driving position and the actual driving time of the piston; comparing the reference driving profile with the actual driving profile; and determining based on a result of the comparing whether the dispensing is proper or not.

A dispensing apparatus according to still another aspect of the present invention includes a syringe which has a piston, the syringe sucking and discharging the liquid; and a driving controller which adapts to an individual difference of the dispensing apparatus and which controls driving of the piston based on a reference driving profile including at least one of a drive starting position and a drive stopping position according to a target dispensing amount.

A dispensing method according to still another aspect of the present invention is for dispensing a liquid in a dispensing apparatus in which a syringe having a piston, the syringe sucking and discharging the liquid, and includes controlling driving of the piston based on a reference driving profile including at least one of a drive starting position and a drive stopping position according to a target dispensing amount, so as to adapt to an individual difference of the dispensing apparatus.

An analyzer according to still another aspect of the present invention includes the dispensing apparatus, wherein the dispensing apparatus according to the present invention.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An exemplary dispensing apparatus, dispensing method, and analyzer of the present invention will be described in detail below with reference to the accompanying drawings.

The invention in its broader aspects is not limited to the specific details and representative embodiments shown and described herein.

Figure 1:
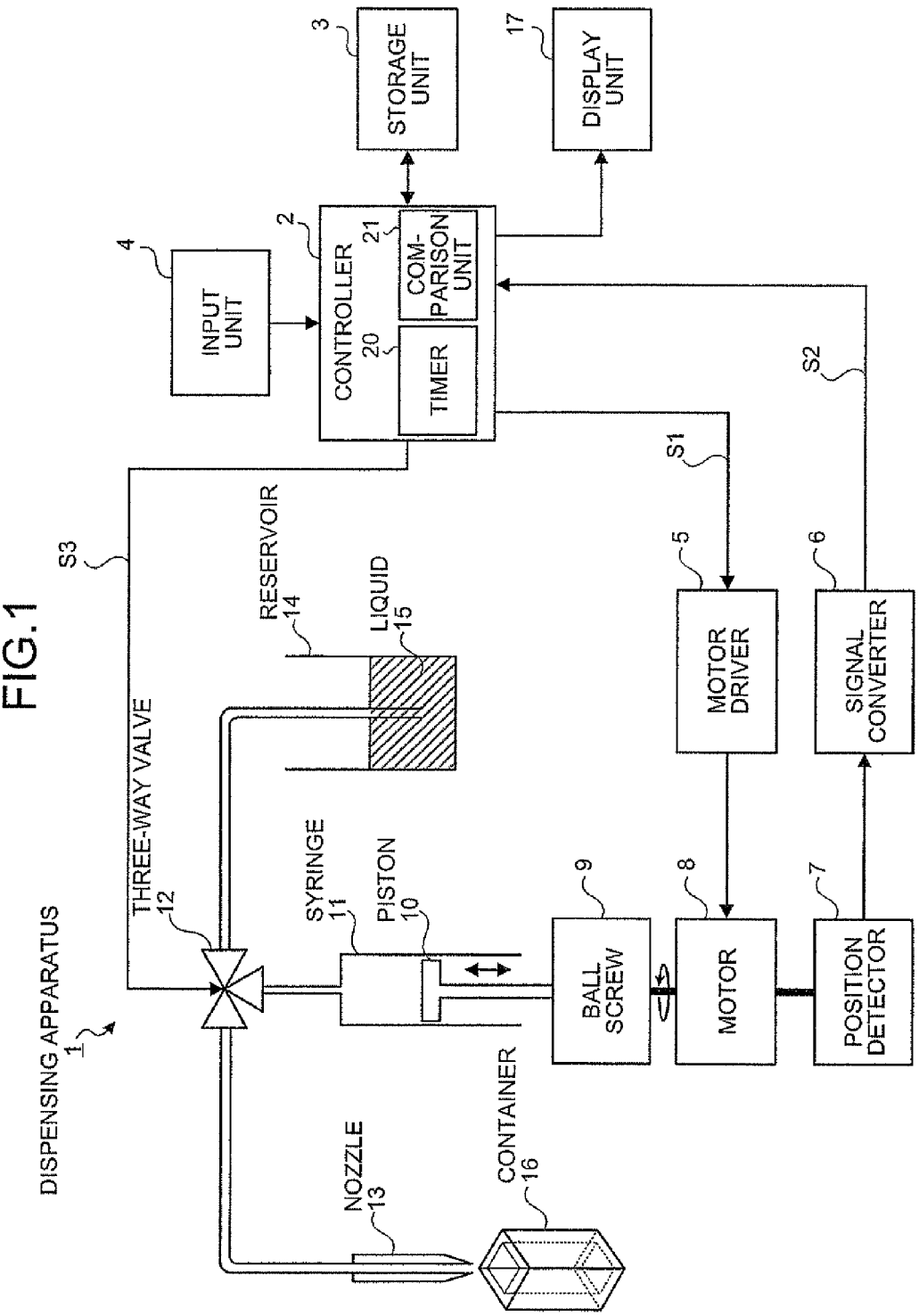
FIG. 1 is a block diagram of a schematic structure of a dispensing apparatus according to an embodiment of the present invention.

FIG. 1 is a block diagram showing schematic elements of a dispensing apparatus 1. The dispensing apparatus 1 includes a controller 2 which controls dispensing motion, a storage unit 3 which stores a reference driving profile including a motion starting position of a piston 10, a motion stopping position of a piston 10, a viscosity of a liquid 15, and a dispensing amount of a liquid 15 as a table, an input unit 4 which inputs the viscosity and the amount of the liquid 15 dispensed, and a display unit 17 which displays whether or not a dispensing is valid. The dispensing apparatus 1 also includes a motor driver 5 which receives a control signal S1 from the controller 2 and controls a drive of a motor 8, the motor 8 which is driven by the motor driver 5, a position detector 7 which detects a position of the piston 10 with reference to a syringe 11 based on a rotational position of the motor 8, a signal converter 6 which converts the position detected by the position detector 7 into a detected signal S2, a ball screw 9 which converts a rotary motion of the motor 8 into a linear motion, the piston 10 which engages to the ball screw 9, the syringe 11 which houses the piston 10, a reservoir 14 which stores the liquid 15, a three-way valve 12 which receives a selection signal S3 from the controller 2 and selectively opens a passage from/to the syringe 11, and a nozzle 13 which discharges the liquid 15 into a container 16.

Also, the controller 2 includes a timer 20 which measures a driving time of the piston 10 and a comparison unit 21 which compares an actual driving profile with the reference driving profile stored in the storage unit 3.

Here, a dispensing motion of the dispensing apparatus 1 is explained. First, when the viscosity and the dispensing amount of the liquid 15 are input through the input unit 4, the controller 2 extracts a table corresponding to the viscosity and the dispensing amount from the storage unit 3.

The controller 2 sends the selection signal S3 to the three-way valve 12 and connects a suction opening of the three-way valve 12 to the reservoir 14. Subsequently, the controller 2 sends the control signal S1 to the motor driver 5 to drive the motor 8. Consequently, the piston 10 of the dispensing apparatus 1 moves to the motion starting position recorded in the table, and the syringe 11 sucks the liquid 15 from the reservoir 14.

Next, the controller 2 sends the selection signal S3 to the three-way valve 12 and connects the suction opening of the three-way valve 12 to the syringe 12, as well as the controller 2 sends the control signal S1 to the motor driver 5 and drives the piston 10 according to the reference driving profile recorded in the table. The reference driving profile is set for a moving distance of the piston 10, which the piston 10 moves until it firstly reaches a zero velocity after starting to move, falls within a predetermined range. Furthermore, a time period which the piston 10 takes to firstly reaches a zero velocity after starting to move or a moving velocity with acceleration and deceleration for the time period is set to fall within a predetermined range.

Figures 2, 3:
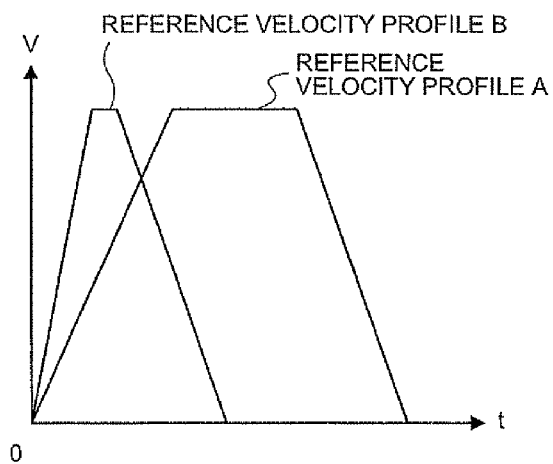
FIG. 2 illustrates specific contents of a table according to the embodiment of the present invention.
FIG. 3 illustrates a reference velocity profile according to the embodiment of the present invention.

The reference driving profile stored in the storage unit 3 is now explained below. FIG. 2 is a view showing a frame format of the reference driving profile recorded in the tables T1 to Tn. As shown in FIG. 2, the tables T1 to Tn are created for different viscosities of the liquid 15, and each table contains the reference driving profile that is the moving distance, the motion starting position, the motion stopping position, and a reference velocity profile for different dispensing amounts.

The moving distance indicates a distance which the piston 10 moves, and the motion starting position indicates a starting position of the piston 10, with reference to the syringe 11, detected by the position detector 7. Also, the motion stopping position indicates a stopping position of the piston 10, with reference to the syringe 11, detected by the position detector 7. The reference driving profile indicates a pattern of a velocity change from the start of the piston 10 to the stop of the piston 10.

The reference driving profile for the piston 10 with the syringe 11 of an inner diameter of 0.2 mm is recorded in the table T1 to Tn. For example, the reference driving profile for the piston 10 dispensing a liquid with a viscosity of 1.0 (mPa·s) is recorded in the table T1. In the table T1, a line of a dispensing amount of 90 (nL) indicates that the apparatus can dispense an amount of 90 (nL) by moving the piston 10 from the motion starting position of 5 to the motion stopping position of 7.86 according to a reference velocity profile A.

Likewise, a line of a dispensing amount of 10 (nL) indicates that the apparatus can dispense an amount of 10 (nL) by moving the piston 10 from the motion starting position of 1 to the motion stopping position of 1.32 according to a reference velocity profile B.

As discussed above, the moving distance as well as the motion starting position and the motion stopping position of the piston 10 differs if the dispensing amount differs. Also, according to the position of the piston 10 at rest in the syringe 11, a priority is given to either the motion starting position or the motion stopping position. Therefore, both the motion starting position and the motion stopping position are written in the table T1 to Tn.

When the piston 10 is driven based on the reference driving profile written in the table T1 to Tn, the controller 2 selects at least two of the moving distance, the motion starting position, and the motion stopping position of the piston 10, according to a property (such as the viscosity) and the amount of dispensed liquid. However, in some case, a desired dispensing amount cannot be obtained even though these are selected because the moving velocity of the piston 10 also affects the dispensing amount. Therefore, the reference velocity profile is written in the reference driving profile described in FIG. 2.

Moreover, the moving distance, the motion starting position, the motion stopping position, and the reference velocity profile of the piston 10 are greatly affected by individual difference of the dispensing apparatus 1. The individual difference of the dispensing apparatus 1, in particular, greatly affects an amount of overshoot and undershoot of the piston 15, thus affects a variation of the dispensing amount. Therefore, the tables T1 to Tn of the reference driving profile are created for each dispensing apparatus 1.

When driving the piston 10 according to the table T1 to Tn created for each dispensing apparatus 1 in this way, the controller 2 is controlled according to the reference driving profile A, B shown in FIG. 3. The reference driving profile A is a pattern of a velocity change when dispensing a liquid of 90 (nL), and the reference driving profile B is a pattern of a velocity change when dispensing a liquid of 10 (nL). The reference driving profiles A, B differ in not only the moving distance of the piston 10 but acceleration and overshoot, etc, of the piston 10. This is due to a change in the reference velocity profile based on the dispensing amount and a complete separation of a drop of the liquid 15 from a tip of the nozzle 13.

Figure 4:
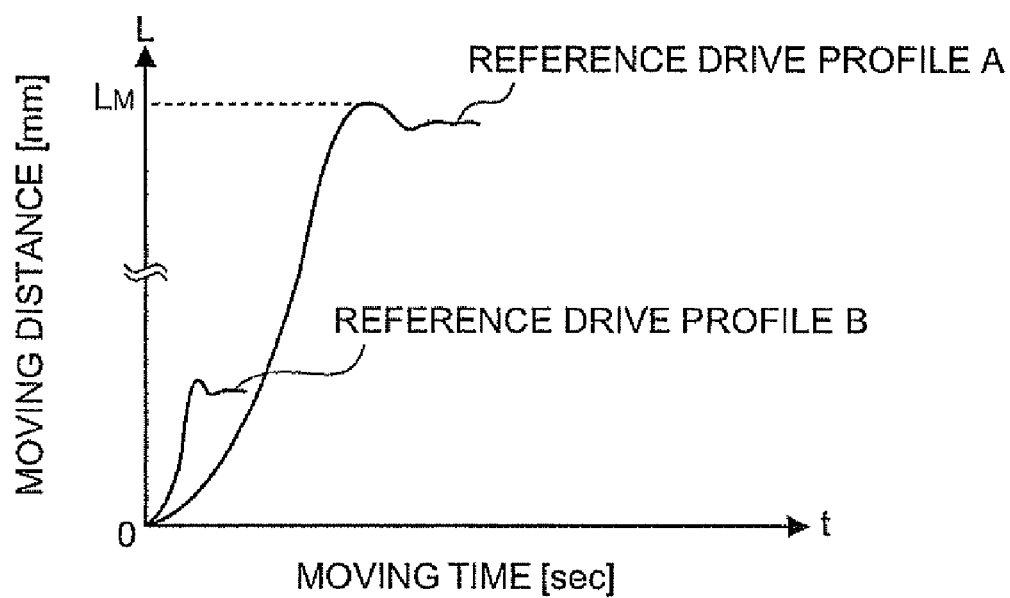
FIG. 4 illustrates a reference driving profile showing a correlation, by an actual measurement, between a driving distance and a driving time of a piston which is driven based on the reference velocity profile shown in FIG. 3.

At this time, the reference velocity profile B which has a less dispensing amount is set to have a greater acceleration (in other words, a greater slop of the line) for driving the piston 10 than the reference velocity profile A which has a larger dispensing amount. FIG. 4 shows the reference driving profiles A, B as a result of an actual measurement showing a relationship between the moving distance (mm) and the moving time (sec) when the piston 10 is actually driven according to the reference velocity profile shown in FIG. 3.

As shown in FIG. 4, the piston 10 repeats some degrees of overshoot and undershoot for a while and finally stops at the motion stopping position, rather than linearly moves to the motion stopping position after starting movement at the motion starting position. Therefore, the actual dispensing amount by driving the piston 10 does not rely on the moving distance of the piston 10 with a linear movement from the motion stating position to the motion stopping position, but, according to FIG. 4 for example, it relies on a moving distance LM which the piston 10 moves until the piston 10 firstly reaches the zero velocity after starting movement. Thus, the table T1 to Tn shown in FIG. 2 are created by considering the overshoot and the undershoot for each dispensing apparatus 1.

The dispensing apparatuses 1 creates the table T1 to Tn about the reference driving profile for each apparatus and stores the table T1 to Tn in the storage unit 3. By driving the piston 10 based on the stored table T1 to Tn, a precise dispensing can be achieved. More specifically, the dispensing apparatus 1 possesses many components, and the characteristic variations of these components cause the variation of the liner movement of the piston 10. Also, a friction between the syringe 11 and the piston 10 varies from position to position; therefore, the performance such as the accuracy of the position determination and the accuracy of the velocity control varies. Thus, a precise dispensing can be achieved by driving the piston 10 based on the stored reference driving profile which is taken the various kinds of variation into account.

In spite of creating the table T1 to Tn about the reference driving profile for each dispensing apparatus 1 and driving the piston 10 based on the stored table T1 to Tn, it is inevitable that in some case an actual dispensing amount differs from an expected dispensing amount. Thus, it is needed to determine a validity of a dispensing action.

For this reason, according to the present invention, the controller 2 creates an actual driving profile of the piston 10 based on the timer 20 and the detected signal S2, as well as the controller 2 drives the piston 10 based on the reference driving profile. The comparison unit 21 determines the validity of the dispensing action by comparing the actual driving profile created in this way to the reference driving profile.

The controller 2 determines the dispensing action is proper and displays a message that the dispensing action is proper on the display unit 17 when the actual driving profile falls within the acceptable range of the reference driving profile base on the result of the comparison by the comparison unit 20. On the other hand, the controller 2 determines the dispensing action is improper and displays a message that the dispensing action is improper on the display unit 17 when the actual driving profile does not fall within the acceptable range of the reference driving profile.

Figure 5:
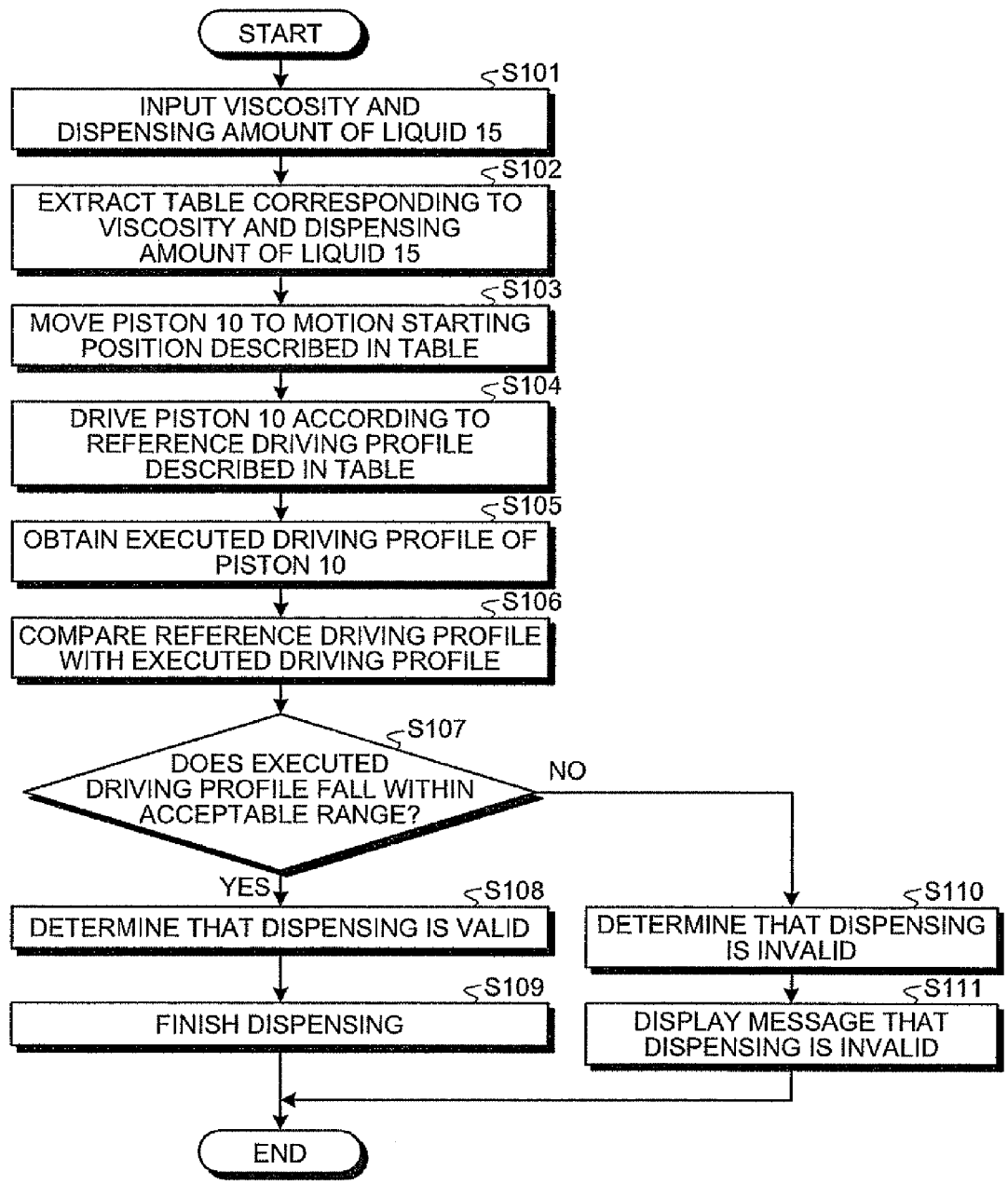
FIG. 5 is a flowchart of a dispensing operation according to the embodiment of the present invention.

The steps of the validity of the dispensing action, performed by the controller 2, are explained below. FIG. 5 is a flow chart showing the dispensing action of the dispensing apparatus 1. As shown in FIG. 5, first of all, the viscosity and the dispensing amount are input in the input unit 4 (step S101). Next, the controller 2 extracts the table corresponding to the input viscosity and dispensing amount from the storage unit 3 (step S102). Then, the controller 2 moves the piston 10 to the motion starting position described in the extracted table (step S103), and the controller 2 drives the piston 10 according to the reference driving profile written in the table (step S104).

Next, controller 2, based on the time which the timer 20 times and the detected signal S2, acquires the actual driving profile which is actually proceeded (step S105). In the following step, the comparison unit 21 compares this actual driving profile to the reference driving profile (step S106). Then the controller 2 determines whether or not the actual driving profile falls within the acceptable range of the reference driving profile (step S107). As a result, when the controller 2 determines that the actual driving profile falls within the acceptable range of the reference driving profile (step S107, Yes), the controller 2 determines that the dispensing action is valid (step S108) and finishes the dispensing action (step S109).

In contrast, when the controller 2 determines that the actual driving profile does not fall within the acceptable range of the reference driving profile (step S107, No), the controller 2 determines that the dispensing action is invalid (step S110) and displays a message that the dispensing action is invalid on the display unit (step S111).

When the controller 2 determines that the dispensing action is invalid, the controller 2 can display a message that dispensing liquid should be discarded or that dispensing action should be taken again on the display unit 17. If the dispensing apparatus 1 has discarding means, the controller 2 can instruct the discarding means to discard with container 16. Instead of displaying the determination result of the validity of the dispensing action on the display unit 17 in the embodiment shown in FIG. 1, it could be substituted by sending an error message from the controller 2 to a control unit of an analyzer which mounts the dispensing apparatus 1 of the present invention when, for example, the dispensing action is invalid.

Also, instead of the reference driving profile in the above-mentioned embodiment including the motion starting position, the motion stopping position, and the reference velocity profile, the reference driving profile can include one of these, and the comparison unit 21 can compare the actual driving profile corresponding to the reference driving profile.

Figure 6:
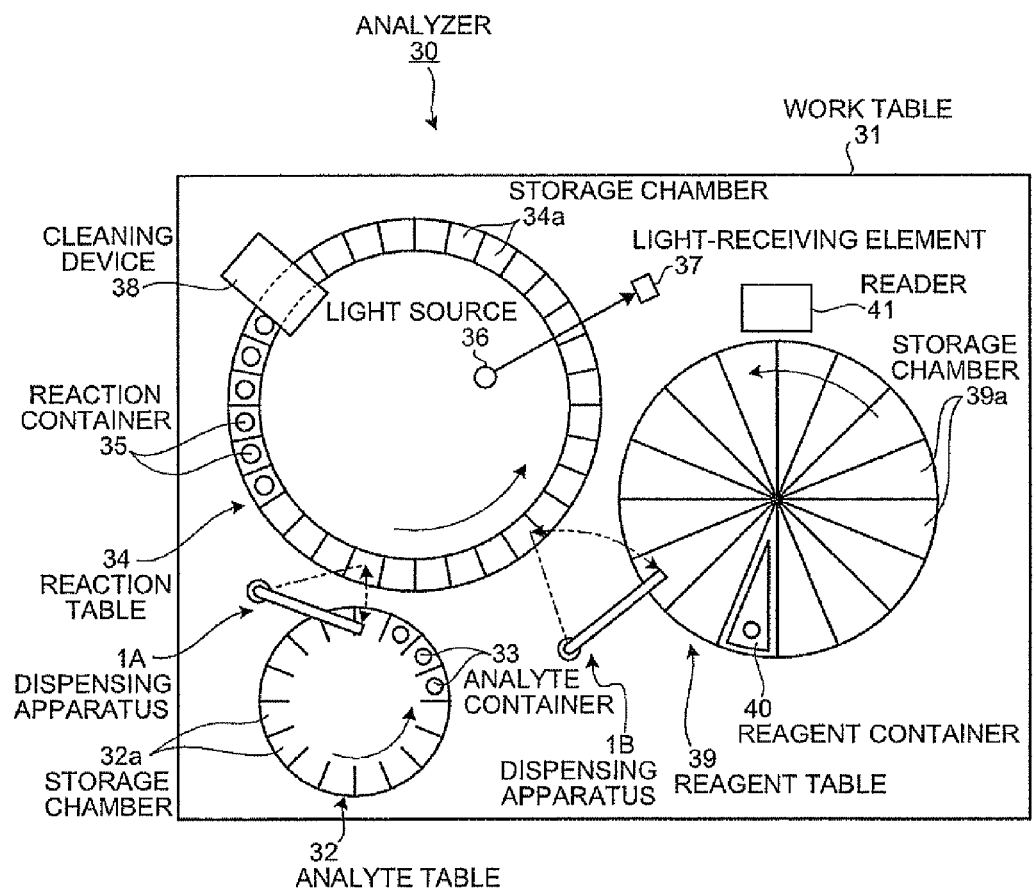
FIG. 6 is a top view of a schematic structure of the dispensing apparatus according to the embodiment of the present invention.

Next, the analyzer having the dispensing apparatus 1 is explained. FIG. 6 is a plan view of the analyzer 30 having the dispensing apparatus 1. As shown in FIG. 6, the analyzer 30 includes a working table 31, and the working table 31 includes an analyte table 32 for receiving an analyte, a reagent table 39 for receiving a regent, a reaction table 34, and dispensing apparatuses 1A, 1B for dispensing the reagent and the analyte respectively.

Also, the working table 31 includes a reader 41 which individually identifies a reagent container 40 accommodated in the reagent table 39, a light source 36 which irradiates the reaction container 35, in which the reagent and the analyte are mixed, with an analyzing light, a light-receiving element 37 which receives the analyzing light passing through the reaction container 35, and a cleaning device 38 which cleans the reaction container 35 after the analysis. Upon the analyzer, the dispensing apparatuses 1A, 1B drive the pistons 10 with the three-way valves 12 being communicated with the nozzles 13, and perform suction and discharge of a desired amount of the reagent or the analyte through the tip of the nozzles 13. At this time, the liquid 15 in the reservoir 14, which is liquid, water, or cleaner unreactive to the reagent and the analyte, fills a passage including the syringe 11 and cleans the inside of the nozzle 13 after discharge of the reagent or the analyte.

The dispensing apparatus 1A sucks the analyte from an analyte container 33 accommodated in a receiving room 32a of the analyte table 32, and discharges the analyte into the reaction container 35 accommodated in a receiving room 34a of the reaction table 34. The dispensing apparatus 1B sucks the reagent from a reagent container 40 accommodated in a receiving room 39a of the reagent table 39, and discharges the reagent into the reaction container 35. The discharged reagent reacts with the discharged analyte in the reaction container 35 while being transported along the circumference direction of the rotating reaction table 34. The reaction liquid of the reagent and the analyte is measured by the light which is irradiated by the light source 36 and received by the light-receiving element 37.

Since the dispensing apparatuses 1A, 1B separately drive pistons 10 respectively base on the reference driving profile corresponding to the dispensing amount, the desired amount can be certainly dispensed, and also since the controller 2 separately determines the validity of the dispensing action by comparing the actual driving profile to the reference driving profile, the dispensing accuracy can be kept uniform. Therefore, the analyzer 30 can correctly analyze the analyte with a uniform analytical accuracy.

In this embodiment, the analyzer can correctly dispenses the liquid and can keep dispensing accuracy uniform by determining the validity of the dispensing action by comparing the actual driving profile to the reference driving profile stored in the storage unit 3. Also, the analyzer can include a feeder and a discharger of the reaction container 35 instead of the cleaning device 38 in FIG. 6, and in this case, the reaction container does not remain in the analyzer 30 after the analysis and is discharged to the outside of the analyzer 30.

Although the storage unit 3 creates the table T1 to Tn for each viscosity of the liquid 15 in this embodiment, the storage unit 3 can create the table according to the other properties of the liquid 15. As an example of the other properties of the liquid 15, a viscosity calculated from a surface tension or a temperature of the liquid are cited. Also, all reference driving profile can be written in one table instead of writing the reference driving profile in each table of each viscosity. Furthermore, the acceptable range of the reference driving profile for the actual driving profile can be changed according to the dispensing amount.

To handle the change in individual characteristics with time of the dispensing apparatus 1, the analyzer can be adapted to periodically update the reference driving profile. Also, the analyzer can be adapted to update the reference driving profile for any mechanical fluctuation which is expected to occur when shipping the device, installing the device, booting the device, marinating the device, and etc. Moreover, the reference driving profile can be created by conducting an experiment of dispensing using an actual liquid or by conducting a simulation. The reference driving profile can be also created by conducting both an experiment of dispensing using an actual liquid and a simulation.

In this embodiment, the storage unit 3 stores therein all of the motion starting position, the motion stopping position, and the reference driving profile, however, the storage unit 3 can be adapted to store one of these and to determine the validity of the dispensing action by comparing the executed driving profile to the reference driving profile of the one of these.

Next, a first modification of the embodiment is explained. While the position detector 7 detects the rotational position of the motor 8 to indirectly detect the position of the piston 10 in the embodiment, the first modification disposes the position detector on the axis of the piston 10 to directly detect the position of the piston 10.

Figure 7:
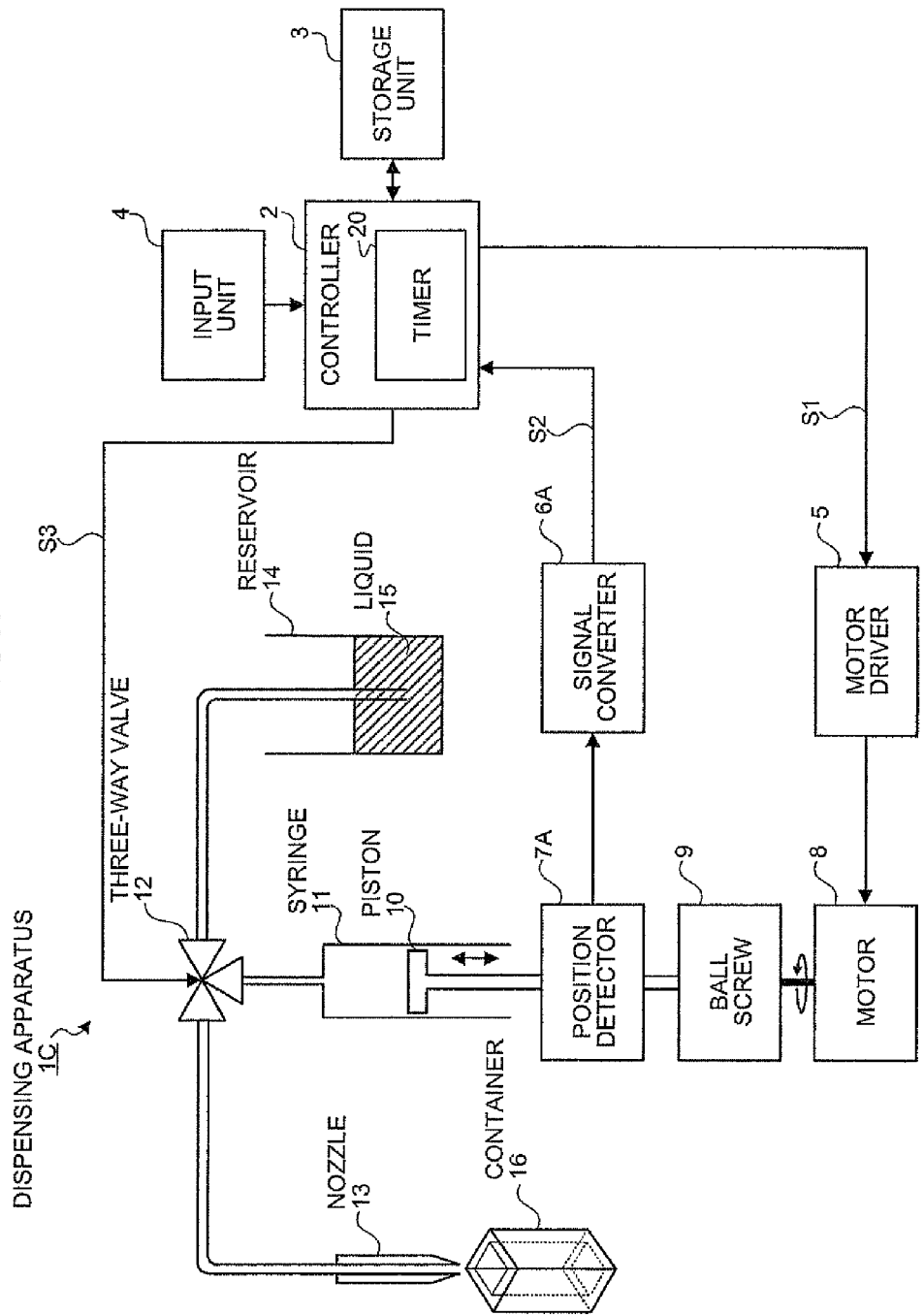
FIG. 7 is a block diagram of a schematic structure of a dispensing apparatus according to a first modification of the embodiment of the present invention.

FIG. 7 is a block diagram showing components of a dispensing device 1C of the first modification of this embodiment. As shown in FIG. 7, the dispensing device 1C uses a position detector 7A instead of the position detector 7 indicated in the embodiment, and uses a signal detector 6A instead of the signal detector 6. Meanwhile, the same reference numerals used in the dispensing device 1 are inhered for the components of the dispensing device of the modifications including the first modification, which will be explained below.

The position detector 7A is disposed between the ball screw 9 and the piston 10 to directly detect the position of the piston 10, and send the position of the piston 10 as the detecting signal S2 to the controller 2. The controller 2 creates the reference driving profile of the piston 10 based on the detecting signal S2 and the time measured by the timer 20, and stores the created reference driving profile in the storage unit 3. The controller 2 feedback controls the piston 10 with the control signal S1 and the detecting signal S2, based on the reference driving profile stored in the storage unit 3.

Since the position detector 7A directly detects the position of the piston 10 in the first modification, it is provided that the reference driving profile can be precisely created without a looseness between the ball screw 9 and the motor 8, and that the precise feedback control of the piston 10 can be made. Additionally, the ball screw 9, which is shown in the embodiment of FIG. 1 and the modification of FIG. 7, can be replaced by a rack-and-pinion for the motion conversion mechanism which converts rotational motion into linear motion.

Next, a second modification of the embodiment is explained. While the piston 10 is driven by the motor 8 and the ball screw 9 in the embodiment and the first modification, the piston 10 is driven by a linear motor in the second modification.

Figure 8:
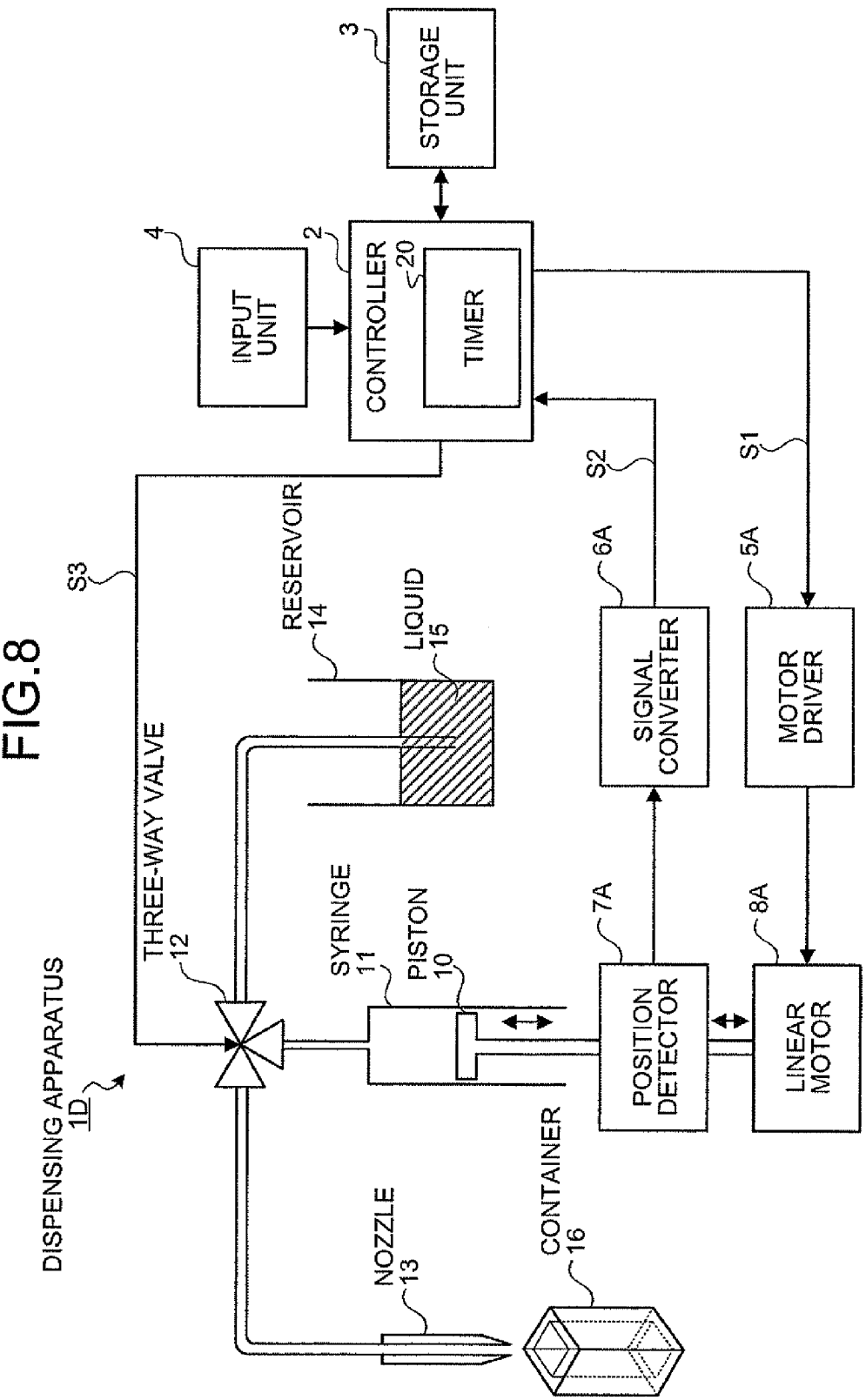
FIG. 8 is a block diagram of a schematic structure of a dispensing apparatus according to a second modification of the embodiment of the present invention.

FIG. 8 is a block diagram showing components of a dispensing device 1D of the second modification of this embodiment. As shown in FIG. 8, the dispensing device 1D uses a linear motor 8A instead of the motor 8 indicated in the first modification, and uses a motor driver 5A instead of the motor driver 5.

The controller 2 controls the motor driver 5A based on the control signal S1, and the motor driver 5A drives the linear motor 8A based on the control signal S1. The linear motor 8A and the piston 10 are directly coupled, and the position detector 7A is disposed between the linear motor 8A and the piston 10 to directly detect the position of the piston 10.

In the second modification, the motion conversion mechanism which converts rotational motion into linear motion can be omitted since the piston 10 is driven by the linear motor 8A. Therefore, a precise driving and a downsizing are provided by eliminating a looseness caused by the motion conversion mechanism.

If a conventional method, which determines a validity of dispensing action by capturing an image of a liquid drop discharged from a tip of a nozzle, is employed, problems would arise from its complexity of the dispensing apparatus caused by existence of an image analysis device and from a difficulty of analysis of a dispensing amount caused by uneven shapes of the liquid drops. However, with the embodiment discussed above, there is no need for capturing the image of the liquid drops, thus the problems are eliminated.

Also, a conventional dispensing apparatus, which dispenses by using a syringe having a piston, has a problem that the dispensing amount varies if an individual difference of a dispensing apparatus and a friction between the syringe and the piston are not taken into consideration. However, according to the above-discussed embodiment, the validity of the dispensing action is determined by comparing the actual driving profile to the reference driving profile stored in the storage unit 3. Thus, the dispensing apparatus according to the present invention can eliminate the problem that the individual difference of the dispensing apparatus and the friction between the syringe and the piston must be taken into consideration, dispense the liquid accurately without an effect of an unevenness of the dispensing liquid amount, and keep the accuracy of dispensing action even.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dispensing apparatus comprising:
    a syringe which has a piston, the syringe adapted to suck and discharge a liquid;
    a storage unit which stores therein a reference driving profile indicating a reference for a driving position of the piston and a driving time of the piston;
    a position detector which detects an actual driving position of the piston;
    a timer which measures an actual driving time of the piston;
    a driving controller which controls driving of the piston based on the reference driving profile, the driving controller creating an actual driving profile based on the actual driving position and the actual driving time of the piston, and the driving controller comparing the reference driving profile with the actual driving profile to determine based on a result of the comparing whether the actual dispensing is proper or not;
    wherein the comparison of the reference driving profile to the actual driving profile indicates a variation of a property of the dispensing apparatus regarding a dispensing accuracy, and the variation of a property of the dispensing apparatus indicates a variation of performance including a positioning accuracy and a velocity control accuracy of the piston; and
    a display which displays a message, the message indicating whether actual dispensing is proper or improper.

2. The dispensing apparatus according to claim 1, wherein the reference driving profile includes at least one of the driving position of the piston, the driving time of the piston, a position at which the piston is located a predetermined time after the piston is started, and a driving velocity of the piston corresponding to the driving position and the driving time.

3. The dispensing apparatus according to claim 1, wherein the reference driving profile indicates a moving distance of the piston within a predetermined range when a driving velocity of the piston firstly reaches zero after the driving of the piston is started.

4. The dispensing apparatus according to claim 3, wherein the reference driving profile indicates a time required for the piston when a velocity of the piston firstly reaches zero after the driving of the piston is started or a velocity, an acceleration and a deceleration of the piston.

5. The dispensing apparatus according to claim 1, wherein the actual dispensing is not proper if the actual driving profile does not fall within an acceptable range of the reference driving profile.

6. The dispensing apparatus according to claim 1, wherein if the actual dispensing is not proper, the message indicates that a dispensing liquid obtained by the dispensing should be discarded or that a dispensing action should be taken again.

7. The dispensing apparatus according to claim 1, further comprising:
    a discarding unit which discards a dispensing liquid obtained by the actual dispensing in response to an instruction of the driving controller if the actual dispensing is not proper.

8. A dispensing method for dispensing a liquid, in which a syringe having a piston, the syringe sucking and discharging the liquid, the dispensing method comprising:
    storing a reference driving profile indicating a reference for a driving position of the piston and a driving time of the piston;
    detecting an actual driving position of the piston;
    a measuring step of measuring an actual driving time of the piston;
    controlling driving of the piston based on the reference driving profile;
    creating an actual driving profile based on the actual driving position and the actual driving time of the piston;
    comparing the reference driving profile with the actual driving profile;
    determining based on a result of the comparing whether the actual dispensing is proper or not;
    wherein the comparing of the reference driving profile to the actual driving profile indicates a variation of a property of the dispensing apparatus regarding a dispensing accuracy, and the variation of a property of the dispensing apparatus indicates a variation of performance including a positioning accuracy and a velocity control accuracy of the piston; and
    displaying a message, the message indicating whether actual dispensing is proper or improper.

9. The dispensing method according to claim 8, wherein the actual dispensing is not proper if the actual driving profile does not fall within an acceptable range of the reference driving profile.

10. The dispensing method according to claim 8, wherein if the actual dispensing is not proper, the message indicates that a dispensing liquid obtained by the dispensing should be discarded or that a dispensing action should be taken again.

11. The dispensing method according to claim 8, further comprising:
    discarding a dispensing liquid obtained by the actual dispensing in response to an instruction of the driving controller if the actual dispensing is not proper.

12. An analyzer comprising a dispensing apparatus, wherein the dispensing apparatus comprises:
    a syringe having a piston, the syringe adapted to suck and discharge a liquid;
    a storage unit which stores therein a reference driving profile indicating a reference for a driving position of the piston and a driving time of the piston;
    a position detector which detects an actual driving position of the piston;
    a timer which measures an actual driving time of the piston;
    a driving controller which controls driving of the piston based on the reference driving profile, the driving controller creating an actual driving profile based on the actual driving position and the actual driving time of the piston, and the driving controller comparing the reference driving profile with the actual driving profile to determine based on a result of the comparing whether the dispensing is proper or not;

wherein the comparison of the reference driving profile to the actual driving profile indicates a variation of a property of the dispensing apparatus regarding a dispensing accuracy, and the variation of a property of the dispensing apparatus indicates a variation of performance including a positioning accuracy and a velocity control accuracy of the piston; and a display which displays a message, the message indicating whether actual dispensing is proper or improper.

13. The analyzer according to claim 12, wherein the actual dispensing is not proper if the actual driving profile does not fall within an acceptable range of the reference driving profile.

14. The analyzer according to claim 12, wherein if the actual dispensing is not proper, the message indicates that a dispensing liquid obtained by the dispensing should be discarded or that a dispensing action should be taken again.

15. The analyzer according to claim 12, further comprising:

a discarding unit which discards a dispensing liquid obtained by the actual dispensing in response to an instruction of the driving controller if the actual dispensing is not proper.

16. The analyzer according to claim 12, further comprising:

a control unit to which the driving controller sends an error message if the actual dispensing is not proper.

17. A dispensing apparatus comprising:

a syringe which has a piston, the syringe adapted to suck and discharge a liquid; and a driving controller which adapts to an individual difference of the dispensing apparatus and which controls driving of the piston based on a reference driving profile including at least one of a drive starting position and a drive stopping position according to a target dispensing amount;

wherein the individual difference indicates a variation of a property of the dispensing apparatus regarding a dispensing accuracy, and the variation of a property of the dispensing apparatus indicates a variation of performance including a positioning accuracy and a velocity control accuracy of the piston.

18. The dispensing apparatus according to claim 17, further comprising:

a position detector which detects a driving position of the piston; and a timer which measures a driving time of the piston, wherein the driving controller feedback controls the driving of the piston based on the driving position detected by the position detector and the driving time measured by the timer.

19. The dispensing apparatus according to claim 17, further comprising:

a storage unit which stores therein the reference driving profile in advance.

20. The dispensing apparatus according to claim 19, wherein the reference driving profile stored in the storage unit in advance is obtained at least one of before the dispensing apparatus is shipped, when the apparatus is installed, when the apparatus is started, and when the dispending apparatus is maintained.

21. The dispensing apparatus according to claim 17, wherein the storage unit includes a plurality of the reference driving profiles for respective different liquids.

22. The dispensing apparatus according to claim 21, wherein the plurality of the reference driving profiles for respective different liquids are the reference driving profiles of physical properties of the liquids including viscosity and surface tension.

23. A dispensing method for dispensing a liquid in a dispensing apparatus in which a syringe having a piston, the syringe sucking and discharging, sucks and discharges the liquid, the dispensing method comprising:

controlling driving of the piston based on a reference driving profile including at least one of a drive starting position and a drive stopping position according to a target dispensing amount, so as to adapt an individual difference of the dispensing apparatus;

wherein the individual difference indicates a variation of a property of the dispensing apparatus regarding a dispensing accuracy, and the variation of a property of the dispensing apparatus indicates a variation of performance including a positioning accuracy and a velocity control accuracy of the piston.

24. The dispensing method according to claim 23, further comprising:

detecting a driving position of the piston;

measuring a driving time of the piston; and feedback controlling driving of the piston based on the detected driving position and the measured driving time.

25. An analyzer comprising a dispensing apparatus, wherein the dispensing apparatus comprises:

a syringe which has a piston, the syringe adapted to suck and discharge a liquid; and a driving controller which adapts to an individual difference of the dispensing apparatus and which controls driving of the piston based on a reference driving profile including at least one of a drive starting position and a drive stopping position according to a target dispensing amount;

wherein the individual difference indicates a variation of a property of the dispensing apparatus regarding a dispensing accuracy, and the variation of a property of the dispensing apparatus indicates a variation of performance including a positioning accuracy and a velocity control accuracy of the piston.

* * * * *